(12) United States Patent
Wenzel et al.

(10) Patent No.: US 10,433,802 B2
(45) Date of Patent: Oct. 8, 2019

(54) AMYLOID PET BRAIN SCAN QUANTIFICATION BASED ON CORTICAL PROFILES

(71) Applicant: KONINKLIJKE PHILIPS N.V., Eindhoven (NL)

(72) Inventors: Fabian Wenzel, Hamburg (DE); Stewart Young, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 938 days.

(21) Appl. No.: 14/893,091

(22) PCT Filed: Jun. 6, 2014

(86) PCT No.: PCT/EP2014/061807
§ 371 (c)(1),
(2) Date: Nov. 23, 2015

(87) PCT Pub. No.: WO2014/195448
PCT Pub. Date: Dec. 11, 2014

(65) Prior Publication Data
US 2016/0128660 A1 May 12, 2016

(30) Foreign Application Priority Data

Jun. 7, 2013 (EP) .................................. 13171034

(51) Int. Cl.
*A61B 6/00* (2006.01)
*A61B 6/03* (2006.01)
(Continued)

(52) U.S. Cl.
CPC .............. *A61B 6/501* (2013.01); *A61B 6/037* (2013.01); *A61B 6/463* (2013.01); *A61B 6/467* (2013.01);
(Continued)

(58) Field of Classification Search
CPC ......... A61B 6/501; A61B 6/037; A61B 6/463; A61B 6/467
See application file for complete search history.

(56) References Cited

U.S. PATENT DOCUMENTS

2004/0267122 A1* 12/2004 Nadadur ................. A61B 8/08
600/440
2010/0055036 A1   3/2010 Suhara et al.
(Continued)

FOREIGN PATENT DOCUMENTS

WO   2005/121796   12/2005
WO   2008/093057    8/2008
(Continued)

OTHER PUBLICATIONS

Camus V et al: "Using PET with F-AV-45 (florbetapir) to quantify brain amyloid load in a clinical environment", European Journal of Nuclear Medicine and Molecular Imaging, Springer, Berlin, vol. 39, No. 4, Jan. 18, 2012.
(Continued)

*Primary Examiner* — Joseph M Santos Rodriguez

(57) ABSTRACT

A medical system (10) and method detects amyloid brain plaque. A positron emission tomography (PET) image of a brain is received. The PET image is generated from a radiotracer binding to amyloid brain plaque. A cortical profile is generated from the PET image. The cortical profile describes cortical tracer uptake to varying projection depths inside the cortex of the brain. The PET image is quantitatively assessed using the cortical profile and/or at least a portion of the cortical profile is displayed.

20 Claims, 5 Drawing Sheets

(51) Int. Cl.
  *G01R 33/56* (2006.01)
  *A61B 5/055* (2006.01)
  *G01R 33/48* (2006.01)

(52) U.S. Cl.
  CPC .......... *A61B 6/5205* (2013.01); *A61B 6/5217* (2013.01); *G01R 33/5608* (2013.01); *A61B 5/055* (2013.01); *A61B 6/5247* (2013.01); *G01R 33/481* (2013.01)

(56) References Cited

U.S. PATENT DOCUMENTS

2011/0306962 A1* 12/2011 Schoenbach ........... A61B 18/12
 606/34
2014/0226898 A1* 8/2014 Lilja ..................... G06T 7/0014
 382/154

FOREIGN PATENT DOCUMENTS

WO     2011137538     10/2011
WO   WO 2013049684 A1 *  4/2013  ........... G06T 7/0014

OTHER PUBLICATIONS

Barthel, et al., "Individualized quantification of brain β-amyloid burden: results of a proof of mechanism phase 0 florbetaben PET trial in patients with Alzheimer's disease and healthy controls", May 6, 2011; Eur J Nucl Med Mol Imaging (2011) 38:1702-1714.
Edison, et al., "Technical aspects of amyloid imaging for Alzheimer's disease", Alzheimer's Research & Therapy 2011.
Furst et al., "Amyloid-β and Glucose Metabolism in Alzheimer's Disease", Journal of Alzheimer's Disease 26 (2011) 105-116.
Vlassenko, et al., "PET Amyloid-Beta Imaging in Preclinical Alzheimer's Disease", Biochim Biophys Acta. Mar. 2012; 1822(3): 370-379.
Landau, et al., "Amyloid-β Imaging with Pittsburgh Compound B and Florbetapir: Comparing Radiotracers and Quantification Methods", J Nucl Med 2013; 54:70-77.
Minoshima, et al., "A Diagnostic Approach in Alzheimer's Disease Using Three-Dimensional Stereotactic Surface Projections of Flurince-18-FDG PET", The Journal of Nuclear Medicine, vol. 36, No. 7, Jul. 1995.
Jack, et al., "Hypothetical model of Dynamic Biomarkers of the Alzheimer's Pathological Cascade", Lancet Neurol. Jan. 2010; 9(1): 119-28.

* cited by examiner

AMYLOID PET BRAIN SCAN QUANTIFICATION BASED ON CORTICAL PROFILES

CROSS REFERENCE TO RELATED APPLICATIONS

This application is a national filing of PCT application Serial No. PCT/EP2014/061807, filed Jun. 6, 2014, published as WO 2014/195448 A1 on Dec. 11, 2014, which claims the benefit of European Patent Application Number 13171034.5 filed Jun. 7, 2013, which is incorporated herein by reference.

FIELD OF THE INVENTION

The present application relates generally to positron emission tomography (PET). It finds particular application in conjunction with amyloid PET imaging for the diagnosis of Alzheimer's disease, and will be described with particular reference thereto. However, it is to be understood that it also finds application in other usage scenarios and is not necessarily limited to the aforementioned application.

BACKGROUND OF THE INVENTION

Amyloid PET imaging images a radiotracer, such as 18F-AV-45 (a.k.a., Florbetapir F-18), which binds to extra-cellular amyloid brain plaques (i.e., amyloid β (AB) plaque), or hard insoluble protein fragments which lie between nerve cells. These extra-cellular amyloid brain plaques are considered a precursor of Alzheimer's disease. See Clifford R Jack, Jr. et al. Hypothetical model of dynamic biomarkers of the Alzheimer's pathological cascade. Lancet Neurol. 2010 January; 9(1): 119-28. Hence, amyloid PET imaging has a high negative predictive value for Alzheimer's disease if the images are correctly interpreted. Due to the expected increase in dementia incidents in the future, the role of Amyloid PET imaging is expected to increase.

Amyloid PET images can be interpreted by visual inspection. Visual inspection of the images is however hampered by different levels of amyloid tracer non-specific binding in white matter. This requires the reader to carefully inspect the images as to their grey matter uptake only. This is cumbersome and unreliable in the absence of brain tissue information.

With reference to FIGS. 1A and 1B, negative and positive amyloid PET scans, respectively, are shown. A negative amyloid PET imaging scan is a scan where β-amyloid plaque is not present, whereas a positive amyloid PET imaging scan is a scan where β-amyloid plaque is present. The scans were generated using 18F-AV-45. FIG. 1A acts as a control and illustrates that significant unspecific tracer uptake can only be found in white matter for a healthy brain. FIG. 1B illustrates that uptake can be found in white and gray matter for a brain suffering from amyloid plaque burden.

Image quantification can also be used to interpret amyloid PET images. However, image quantification suffers from the same problem of unspecific tracer uptake in white matter as visual inspection. Namely, amyloid images are typically quantified by determining the standardized uptake value ratio (SUVR) in different cortical areas with respect to a reference region, such as the cerebellum. Since unspecific white matter uptake is included in quantification, specificity and sensitivity decrease.

The present application provides a new and improved system and method which overcome the above-referenced problems and others.

SUMMARY OF THE INVENTION

In accordance with one aspect, a medical system for detecting amyloid brain plaque is provided. The medical system includes at least one processor. The at least one processor is programmed to receive a positron emission tomography (PET) image of a brain. The PET image is generated from a radiotracer binding to amyloid brain plaque. The at least one processor is further programmed to generate a cortical profile from the PET image. The cortical profile describes cortical tracer uptake to varying projection depths inside the cortex of the brain. Even more, the at least one processor is further programmed to at least one of: 1) quantitatively assess the PET image using the cortical profile; and 2) display at least a portion of the cortical profile.

In accordance with another aspect, a medical method for detecting amyloid brain plaque is provided. A positron emission tomography (PET) image of a brain is received. The PET image is generated from a radiotracer binding to amyloid brain plaque. A cortical profile is generated from the PET image. The cortical profile describes cortical tracer uptake to varying projection depths inside the cortex of the brain. At least one of: 1) the PET image is quantitatively assessed using the cortical profile; and 2) at least a portion of the cortical profile is displayed.

In accordance with another aspect, a medical system for detecting amyloid brain plaque is provided. The medical system includes an amyloid module configured to receive a positron emission tomography (PET) image of a brain. The PET image is generated from a radiotracer binding to amyloid brain plaque. The amyloid module is further configured to generate cortical surface projections for the varying projection depths from the PET image and generate a cortical profile from the cortical surface projections. The cortical profile describes cortical tracer uptake for varying projection depths inside the cortex of the brain. The amyloid module is further configured to at least one of: 1) quantitatively assess the PET image using the cortical profile; and 2) display at least a portion of the cortical profile.

One advantage resides in improved interpretation of amyloid positron emission tomography (PET) images.

Another advantage resides in less burdensome and more reliable visual inspection of amyloid PET images.

Another advantage resides in improved specificity and sensitivity in quantification of amyloid PET images.

Still further advantages of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE EMBODIMENTS

Figure 1A:
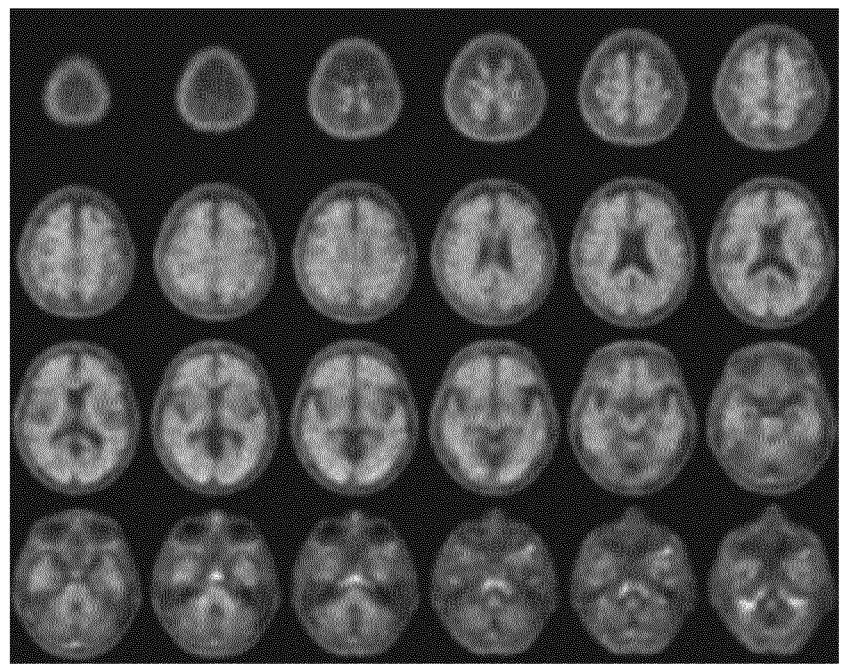
FIG. 1A illustrates a negative amyloid positron emission tomography (PET) scan of a healthy brain.
Figure 1B:
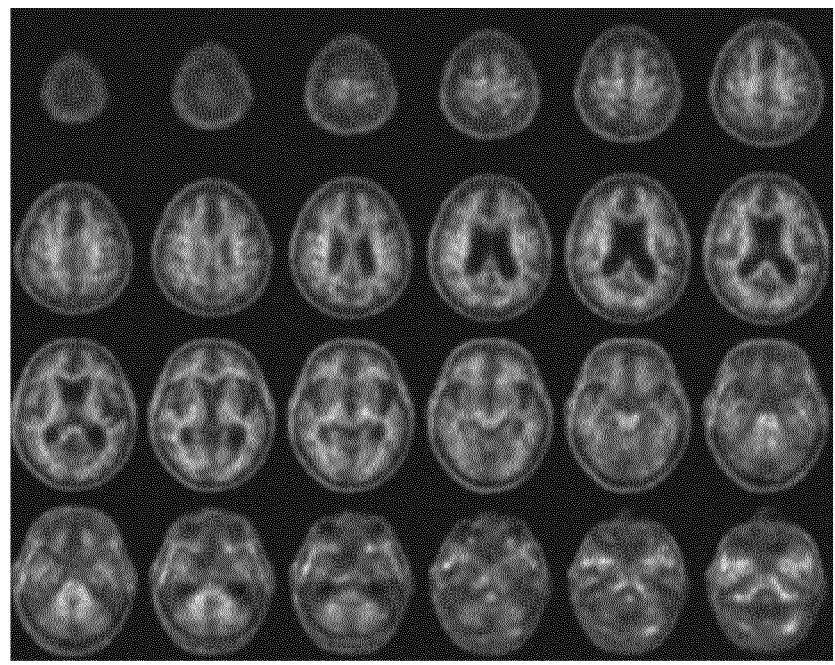
FIG. 1B illustrates a positive amyloid PET scan of a brain suffering from amyloid plaque burden.
Figure 2A:
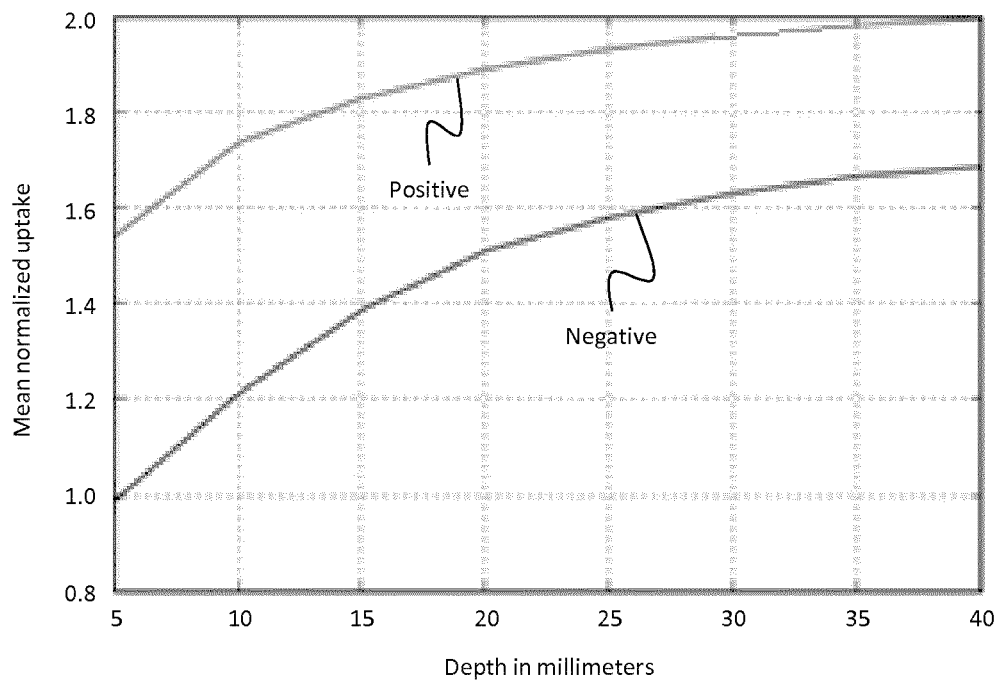
FIG. 2A illustrates a graph of mean normalized tracer uptake against projection depth.
Figure 2B:
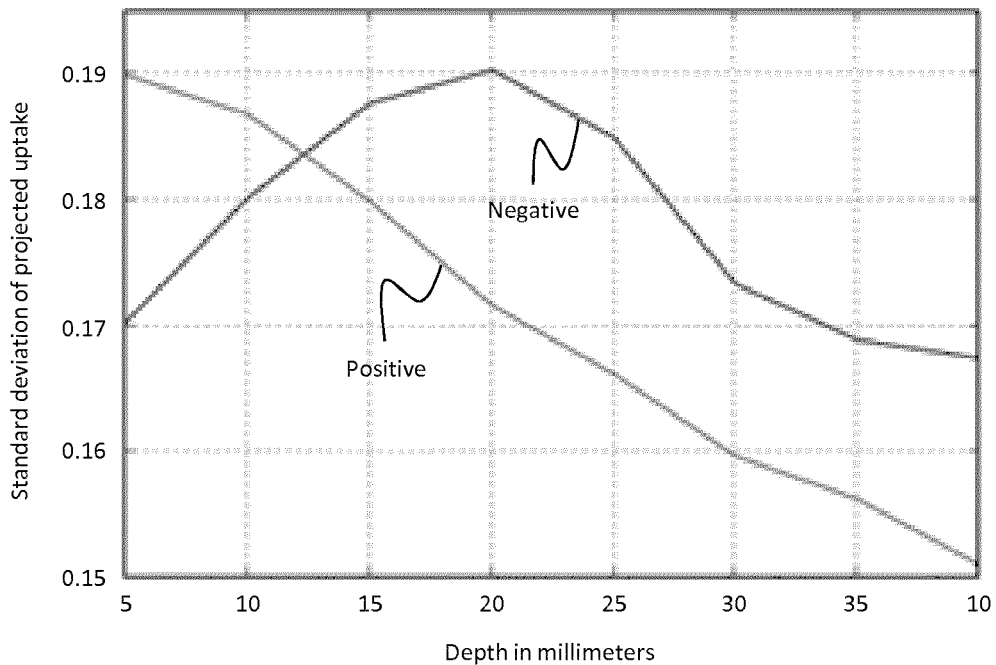
FIG. 2B illustrates a graph of standard deviation of uptake against projection depth.

The present application proposes to improve the quantification of radiotracer uptake in amyloid positron emission tomography (PET) scans by inspecting cortical profiles with the cortical uptake at varying depths inside the cortex. FIGS. 2A and 2B illustrate two examples of cortical profiles. FIG. 2A illustrates a graph of mean normalized tracer uptake (i.e., y-axis) against projection depth (i.e., x-axis), and FIG. 2B illustrates a graph of standard deviation of uptake (i.e., y-axis) against projection depth (i.e., x-axis). The uptake values of FIGS. 2A and 2B correspond to standardized uptake value ratio (SUVR) values with a reference region such as the cerebellum. As can be seen, positive and negative amyloid cases differ markedly. Hence, a clinician viewing a cortical profile and/or feature thereof, such as depth of maximum standard deviation, can make an improved Alzheimer's diagnosis.

Figure 3:
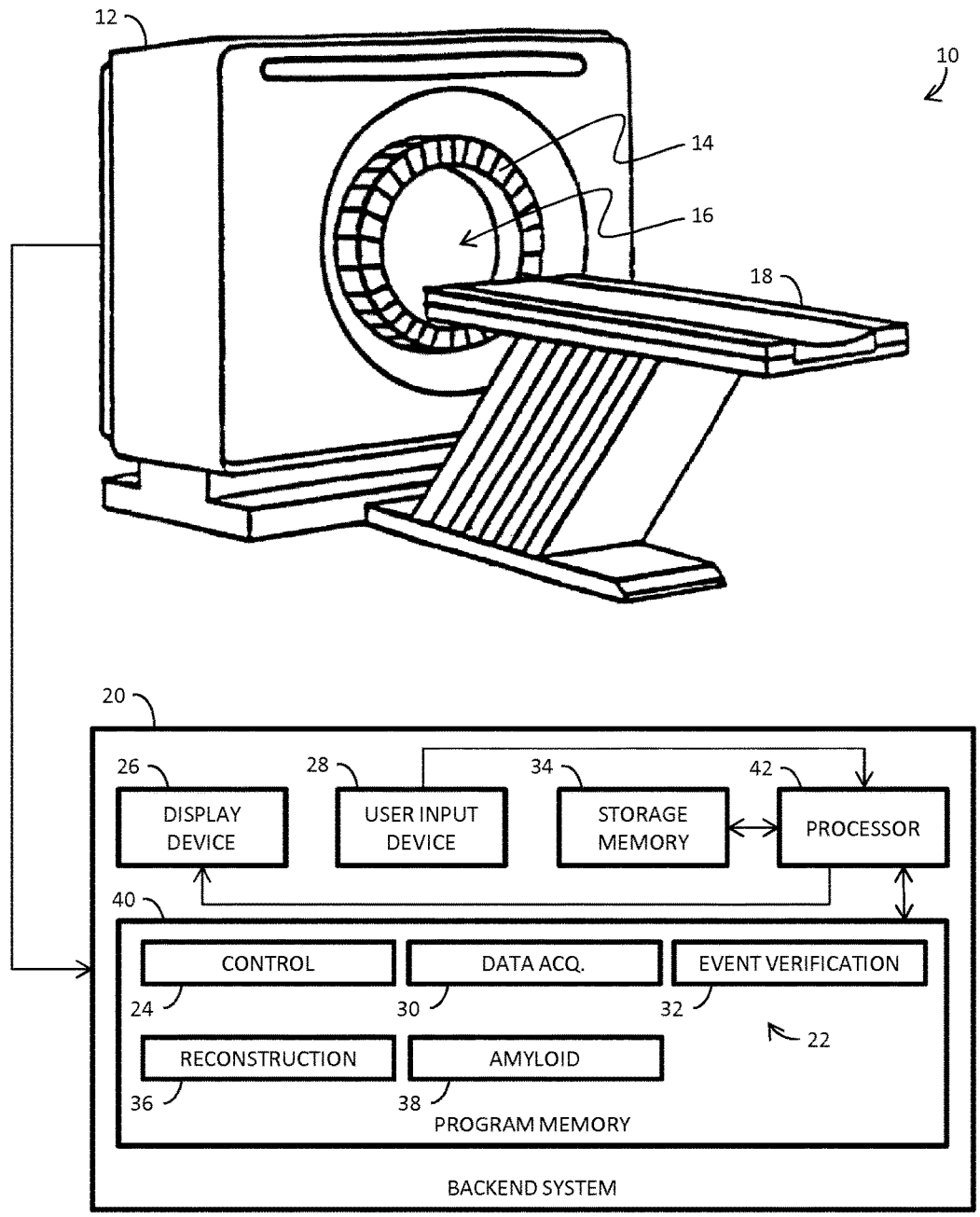
FIG. 3 illustrates a PET imaging system.

With reference to FIG. 3, a positron emission tomography (PET) imaging system 10 includes a scanner 12 to generate raw PET data. The scanner 12 includes detectors 14 arranged around a bore of the scanner 12. The bore defines an examination region 16 for receiving a region of interest (ROI), such as a brain, of a subject to image. The detectors 14 are typically arranged in a stationery ring. However, rotatable heads are also contemplated. The scanner 12 can be mounted on tracks to facilitate patient access. The tracks extend in parallel to a longitudinal axis of a subject support 18 carrying a subject to image. A motor and drive or the like provides longitudinal movement and vertical adjustment of the subject support 18 in the examination region 16.

A backend system 20 generates PET images of ROIs using the scanner 12. Before a PET scan commences, the ROI is injected with a radionuclide which emits positrons and is positioned within the examination volume 16 (e.g., using the subject support 18). Suitably, for amyloid PET imaging, the radionuclide preferentially binds to extra-cellular amyloid brain plaques (i.e., amyloid β (AB) plaque), such as 18F-AV-45 (a.k.a., Florbetapir F-18). The backend system 20 can also be used to quantify amyloid PET images as amyloid positive or amyloid negative, and/or provide tools aiding visual inspection of amyloid PET images, for detecting and/or predicting Alzheimer's disease. The backend system 20 is typically remote from the scanner 12 and includes a plurality of modules 22 to carry out the forgoing functionality.

A control module 24 of the backend system 20 controls overall operation of the backend system 20. The control module 24 suitably displays a graphical user interface (GUI) to a user of the backend system 20 using a display device 26 of the backend system 20. Further, the control module 24 suitably allows the operator to interact with the GUI using a user input device 28 of the backend system 20. For example, the user can interact with the GUI to instruct the backend system 20 to coordinate imaging of a ROI.

A data acquisition module 30 of the backend system 20 controls the scanner 12 to perform PET scans of the ROI. During a PET scan, the data acquisition module 30 monitors each of the detectors 14 for an energy spike (e.g., integrated area under the pulse) indicating an event. A pair of annihilation gammas is produced by a positron annihilation event in the examination region 16, where each annihilation gamma of the pair travels in approximately opposite directions. When a gamma deposits energy in the detectors 14, the data acquisition module 30 detects and time stamps the event. Further, the data acquisition module 30 records an estimate of the location where the event occurred on the detectors 14 and an estimate of the energy of the event.

An event verification module 32 uses emission data from the data acquisition module 30 to detect and verify coincident events. The emission data typically includes time stamps, location estimates and energy estimates for detected events. A coincident event corresponds to the detection of a pair of gammas within a specified time difference of each other, the specified time difference small enough to ensure the gammas are from the same annihilation event. Verified coincident events typically include only gammas falling within a predetermined energy window (e.g., approximately 511 keV) and define lines of response (LORs). The LORs of detected and verified coincident events are typically stored in a list in one of one or more storage memories 34 along with the time stamps of the corresponding gammas.

A reconstruction module 36 of the backend system 20 reconstructs detected and verified LORs into a PET image of the ROI. Any number of well know algorithms for reconstructing the detected and verified LORs into PET images are contemplated. For example, the reconstruction module 36 can be configured to reconstruct the detected and verified LORs into an amyloid PET image. The PET images are suitably stored in one of the storage memories 34.

For the sake of simplicity, random correction, attenuation correction, cascade gamma correction, scatter correction and the like were not discussed. However, it is to be appreciated that such correction can be employed with the PET imagine system 10. For example, the PET imaging system 10 can perform scatter correction by clustering detected events within a specified time window of each other into a common event, the specified time difference being small enough to ensure the detected events are from the same gamma. As another example, statistical approaches to scatter correction using single-scatter simulation (SSS) and/or Monte Carlo simulation are contemplated.

An amyloid module 38 quantifies amyloid PET images as amyloid positive or amyloid negative, and/or provides tools aiding visual inspection of amyloid PET images, using cortical surface projections. A cortical surface projection is a projection of a cortical uptake value inside the cortex to the cortex surface. Cortical surface projections are known for analyzing cortical lesions in PET scans, as described in Satoshi Minoshima et al. A diagnostic approach in Alzheimer's disease using three-dimensional stereotactic surface projections of fluorine-18-FDG PET. J Nucl Med. 1995 July; 36(7): 1238-48. However, cortical surface projections are not known for use in quantifying amyloid PET images as amyloid positive or amyloid negative, and/or providing tools aiding visual inspection of amyloid PET images.

Figure 4:
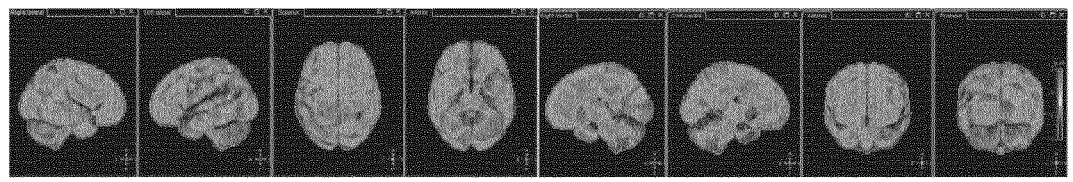
FIG. 4 illustrates a projection image of an amyloid PET scan with a maximum projection depth of 14 millimeters.

Projection images can be generated from the cortical surface projections. A projection image can be determined by projecting points from a maximum depth inside the cortex to the cortex surface. The assigned value for a projected point is then a statistic regarding the uptake values along the ray spanning between the projected point on the cortex surface and its corresponding point at the maximum depth. Such statistics include, for example, standard deviation, maximum, minimum, mean, etc. FIG. 4 illustrates projection images of an amyloid PET scan with a maximum projection depth of 14 millimeters.

The projection images are used to generate cortical profiles. A cortical profile describes cortical uptake at varying depths inside the cortex for a region of the cortex surface. Such regions can include pixels, voxels, image slices, and the like. A cortical profile for a region of the cortex surface can be generated by generating projection images at varying maximum depths for the region. Thereafter, the projection images are combined into the cortical profile. For example, an uptake value is determined for the region in each projection image and the determined values are combined as a function of depth. For a region including a plurality of pixels, a statistic regarding the pixels is used to determine values for the region. Such statistics include, for example, standard deviation, maximum, mean, etc.

FIGS. 2A and 2B illustrate different cortical profiles for a region of a cortical surface. FIG. 2A illustrates a graph of mean normalized tracer uptake (i.e., y-axis) against projection depth (i.e., x-axis), and FIG. 2B illustrates a graph of standard deviation of uptake (i.e., y-axis) against projection depth (i.e., x-axis). The uptake values of FIGS. 2A and 2B correspond to SUVR values with a reference region such as the cerebellum. As can be seen, positive and negative amyloid cases differ markedly. Hence, these cortical profiles and others can be used for quantification of amyloid PET images.

Figure 5A:
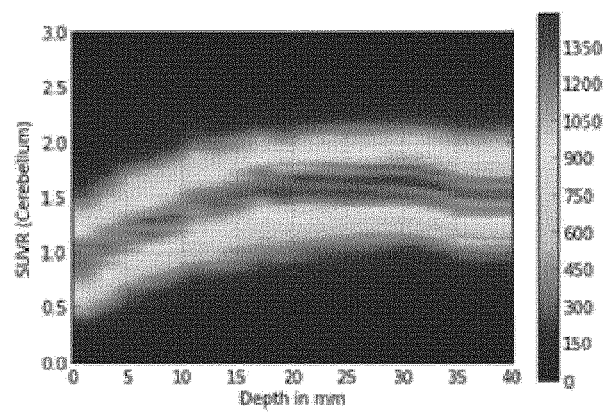
FIG. 5A illustrate an intensity histogram for an amyloid negative scan.
Figure 5B:
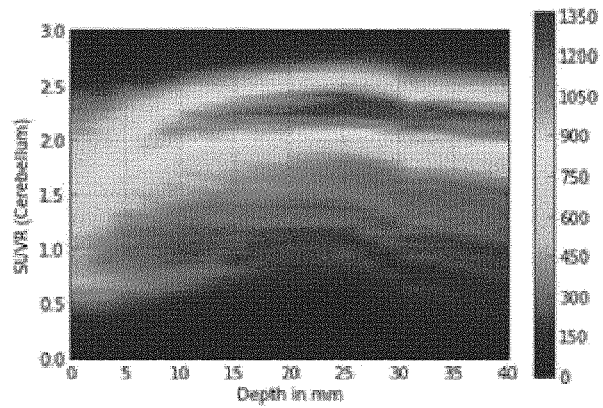
FIG. 5B illustrate an intensity histogram for an amyloid positive scan.

Cortical profiles can also be generated from the cortical surface projections without intermediate projection images. In that regard, the cortical profiles can be simple intensity profiles describing the intensity (i.e., frequencies of combinations of uptake values and depths within the cortex. FIGS. 5A and 5B illustrate intensity histograms for an amyloid negative scan and an amyloid positive scan, respectively, according to cortical surface projection depth. These intensity histograms correspond to the same cortical surface projections as FIGS. 2A and 2B. Further, the uptake values of FIGS. 5A and 5B correspond to SUVR values with the cerebellum as the reference region.

To quantify amyloid PET images as amyloid positive or amyloid negative, image-based features are extracted from cortical profiles of the amyloid PET images. Image-based features can include statistics regarding cortical profiles, such as the depth of the maximum or minimum uptake value. For example, an image-based feature of FIG. 2B suitable for quantifying a PET image includes the depth of a maximum standard deviation. After extracting image-based features (i.e., image-based feature values), the extracted image-based features can be used to classify amyloid PET images as amyloid positive or amyloid negative. Classification can be performed according to any number of well-known approaches. In this way, the cortical profiles open the doors to additional biomarkers for distinguishing between amyloid positive and negative images.

According to one approach to classification, a common feature vector (i.e., one or more features, typically a plurality of features) is extracted from at least one cortical profile of each of a plurality of training amyloid PET images, which include both amyloid positive and amyloid negative images. A machine learning algorithm, typically a supervised machine learning algorithm, such as support vector machine (SVM), is then trained on the extracted feature vectors to distinguish between amyloid positive and amyloid negative. After training the classifier, an amyloid PET image is quantified as amyloid positive or amyloid negative by extracting the common feature vector therefrom and inputting the extracted feature vector to the classifier.

To aid in visual inspection of amyloid PET images, an amyloid PET scan can be displayed to a user of the PET imaging system 10 using the display device 26. The user can then interact with the amyloid PET scan using the user input device 28. Upon selecting a region, such as a pixel or voxel, a corresponding cortical profile can be displayed on the display device 26. For example, upon selection of a region of a PET scan, the corresponding intensity profile for the selected region can be displayed. Alternatively, the global average cortical profile for a PET scan, or one or more regional cortical profiles for the PET scan, can be displayed by default in lieu of the PET scan. For example, the cortical intensity profiles of select regions of the PET image can be displayed.

As an alternative to displaying an entire cortical profile for a region, a portion of a cortical profile can be displayed with a slider bar allowing adjustment of the depth of the cortical profile shown. For example, a portion of a cortical profile corresponding to a selected depth can be displayed. A slider bar can then be used to change the selected depth. Advantageously, this allows patterns of change to be seen in the region of the cortical profile, which are significant in identifying Alzheimer's disease.

Each of the plurality of modules 22 can be embodied by processor executable instructions, circuitry (i.e., processor independent), or a combination of the two. The processor executable instructions are stored on at least one program memory 40 of the backend system 20 and executed by at least one processor 42 of the backend system 20. As illustrated, the plurality of modules 22 is embodied by processor executable instructions. However, as is to be appreciated, variations are contemplated. For example, the data acquisition module 30 can be circuitry.

The foregoing approach to quantifying amyloid PET images as amyloid positive or amyloid negative, and/or providing tools aiding visual inspection of amyloid PET images, can be used with any neurological imaging software supporting amyloid PET. Further, the foregoing approach can advantageously be used in situations where tissue information distinguishing white and gray matter is not available. Even so, it is contemplated that the foregoing approach is used when tissue information is available. Such tissue information can be obtained using a magnetic resonance (MR) system and used to identify gray matter. Quantification can then be performed on the gray matter.

Figure 6:
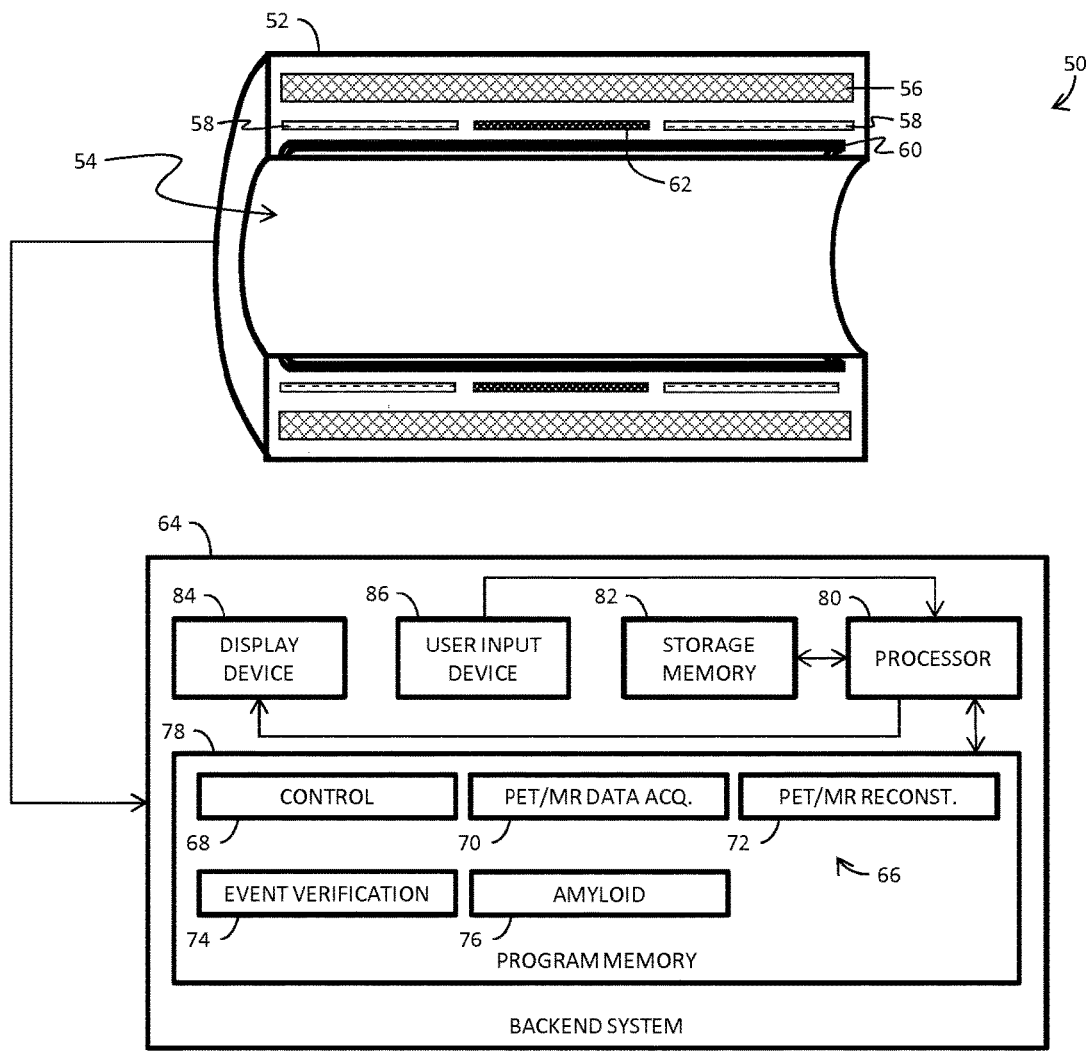
FIG. 6 illustrates a multi-modality imaging system including PET and magnetic resonance (MR) imaging systems.

With reference to FIG. 6, a multi-modality imaging system 50 includes PET and MR systems. The multi-modality imaging system 50 includes a scanner 52 to generate raw PET data and raw MR data. The scanner 52 includes a bore defining an examination region 54 for receiving a ROI, such as a brain, of a subject to image. The scanner 52 can be mounted on tracks to facilitate patient access. The tracks extend in parallel to a longitudinal axis of a subject support carrying a subject to image. A motor and drive or the like provides longitudinal movement and vertical adjustment of the subject support in the examination region 54.

For MR imaging, the scanner 52 includes a main magnet 56 that creates a strong, static $B_0$ magnetic field extending through the examination region 54. Further, the scanner 52 includes a plurality of magnetic field gradient coils 58 to superimpose magnetic field gradients, such as x, y and z gradients, on the static $B_0$ magnetic field in the examination region 54. Even more, the scanner 52 includes one or more transmit coils and one or more receive coils. For example, the transmit coils and the receive coils can share a whole body coil 60. The transmit coils transmit $B_1$ resonance excitation and manipulation radio frequency (RF) pulses into the examination region 54. The receive coils receive spatially encoded magnetic resonance signals from the examination region 54.

For PET imaging, the scanner 52 includes detectors 62 arranged around the bore. The detectors 62 are typically arranged in a stationery ring. However, rotatable heads are also contemplated. As should be the PET scanner 12 of FIG. 3 is generally the same as the scanner 52 except that the scanner 52 further includes the necessary coils and circuitry for generating raw MR data.

A backend system 64 generates PET and MR images of ROIs using the scanner 52. Before a scan, the ROI is positioned within the examination volume 54 (e.g., using the subject support). Further, before a PET scan, the ROI is injected with a radionuclide which emits positrons. Suitably, for amyloid PET imaging, the radionuclide preferentially binds to extra-cellular amyloid brain plaques (i.e., amyloid β (AB) plaque), such as 18F-AV-45 (a.k.a., Florbetapir F-18). The backend system 64 can also be used to quantify amyloid PET images, and/or provide tools aiding visual inspection of amyloid PET images, for detecting and/or predicting Alzheimer's disease. Suitably, gray matter is identified first using corresponding MR images, such that only gray matter is quantified and/or visually inspected.

The backend system 64 is typically remote from the scanner 52 and includes a plurality of modules 66 to carry out the forgoing functionality. The plurality of modules 66 includes a control module 68, a data acquisition module 70, a reconstruction module 72, an event verification module 74 and an amyloid module 76. These modules are suitably as described in connection with the PET imaging system 10 of FIG. 3, except that the data acquisition module 70 is configured to acquire raw PET data and raw MR data using the scanner 52. Further, the reconstruction module 72 is configured to further reconstruct MR data MR images. Even more, the amyloid module 76 is configured to further use MR images to identify gray matter of brains. Quantification of corresponding PET images is then limited to gray matter.

Each of the plurality of modules 66 can be embodied by processor executable instructions, circuitry (i.e., processor independent), or a combination of the two. The processor executable instructions are stored on at least one program memory 78 of the backend system 64 and executed by at least one processor 80 of the backend system 66. As illustrated, the plurality of modules 66 are embodied by processor executable instructions. However, as is to be appreciated, variations are contemplated. One or more storage memories 82 further provide storage for the plurality of modules 66. For example, the memories 82 can provide storage for raw data acquired by the data acquisition module 70. Even more, a display device 84 and user input device 86 allow the plurality of modules 66 to interact with users of the multi-modality imaging system 50.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a controller includes at least one memory and at least one processor, the processor executing processor executable instructions on the memory; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical system for detecting amyloid brain plaque, said medical system comprising:
 a display device;
 at least one processor programmed to:
  receive a magnetic resonance (MR) image of a brain;
  identify gray matter of the brain using the MR image;
  receive a positron emission tomography (PET) image of a brain, the PET image generated from a radiotracer binding to amyloid brain plaque;
  generate a cortical profile for at least a region of the PET image, the cortical profile describing cortical tracer uptake to varying projection depths inside the identified gray matter of the brain;
  extract an image-based feature from the cortical profile;
  classify the brain as amyloid positive or amyloid negative using the extracted feature; and
  control the display device to display the cortical profile for at least the region of the PET image in response to selection of the region by a clinician and whether the brain is classified as amyloid positive or amyloid negative.

2. The medical system according to claim 1, wherein the at least one processor is further programmed to:
 generate cortical surface projections from the PET image, wherein each of the cortical surface projections is a projection of a cortical tracer uptake value from a surface of the cortex to an edge of the gray matter, and wherein the cortical profile is generated from the cortical surface projections.

3. The medical system according to claim 1, wherein the at least one processor is further programmed to:
 generate cortical surface projections at projection depths varying with a depth of the gray matter from the PET image, wherein each of the cortical surface projections is a projection of a cortical tracer uptake value between the depth of the gray matter and a cortex surface of the brain;
 for each of the projection depths, determine a projection image of the cortex surface of the brain from the cortical surface projections, each pixel of the projection image assigned a statistical value describing the distribution of cortical tracer uptake values along a ray extending from a first pixel of the PET image to a second pixel of the PET image, the first pixel corresponding to the pixel of the projection image, and the second pixel being at the projection depth and projecting to the first pixel of the PET image; and combining the projection images to create the cortical profile.

4. The medical system according to claim 1, wherein the cortical profile includes an intensity profile describing the intensity for different combinations of cortical tracer uptake and projection depth and wherein the display is configured to display the intensity profile.

5. The medical system according to claim 1, wherein the cortical profile describes mean normalized uptake, or standard deviation of uptake, for varying projection depths.

6. A medical method for detecting amyloid brain plaque, said medical method comprising:
  receiving a positron emission tomography (PET) image of a brain, the PET image generated from a radiotracer binding to amyloid brain plaque;
  generating a cortical profile from the PET image, the cortical profile describing cortical tracer uptake to varying projection depths inside the cortex of the brain;
  classify the brain of the PET image as amyloid positive or amyloid negative based on the cortical profile; and
  controlling a display to display the classification of the brain and at least one of the PET image and the cortical profile.

7. The medical method according to claim 6, wherein the radiotracer is 18F-AV-45.

8. The medical method according to claim 6, further including:
  generating cortical surface projections at the varying projection depths from the PET image, wherein each of the cortical surface projections is a projection of a cortical tracer uptake value between a projection depth and the cortex surface of the brain, and wherein the cortical profile is generated from the cortical surface projections; and
  controlling the display to a depiction of the cortical surface projections.

9. The medical method according to claim 6, further including:
  receiving a magnetic resonance (MR) image of a brain; and
  identifying gray matter of the brain using the MR image, wherein the cortical profile describes at least a part of the identified gray matter of the brain.

10. The medical method according to claim 6, wherein the cortical profile includes an intensity profile describing the intensity for different combinations of cortical tracer uptake and projection depth.

11. The medical method according to claim 6, wherein the cortical profile describes mean normalized uptake, or standard deviation of uptake, for varying projection depths.

12. At least one processor programmed to perform the method according to claim 6.

13. A non-transitory computer readable medium carrying software which controls one or more processors to perform the method according to claim 6.

14. A medical system for detecting amyloid brain plaque, said medical system comprising:
  an amyloid module, including machine executable instructions and circuitry configured to execute the instructions, configured to:
    receive a positron emission tomography (PET) image of a brain, the PET image generated from a radiotracer binding to amyloid brain plaque;
    generate cortical surface projections for the varying projection depths from the PET image;
    generate a cortical profile from the cortical surface projections, the cortical profile describing cortical tracer uptake for varying projection depths inside the cortex of the brain;
    classify the brain in the PET image as amyloid positive or amyloid negative based on the cortical profile; and
    control a display to display the amyloid positive/negative classification.

15. The medical system according to claim 1, wherein the at least one processor is further programmed to:
  calculate intensity histograms which are used in classifying the brain as amyloid positive or amyloid negative.

16. The medical system according to claim 1, wherein classifying the brain as amyloid positive or amyloid negative includes employing a trained machine learning algorithm to distinguish between amyloid positive and amyloid negative.

17. The medical method according to claim 6, wherein generating the cortical profile includes generating intensity profiles describing frequencies of combinations of uptake values in depth within the cortex.

18. The medical method according to claim 6, wherein classifying the image includes extracting statistics regarding the cortical profiles including a depth of a maximum or a minimum uptake value and a depth of a maximum standard deviation, the extracted statistics being used in classifying the PET images as amyloid positive or amyloid negative.

19. The medical method according to claim 6, wherein classifying the PET image as amyloid positive or amyloid negative includes using a trained machine learning algorithm to extract feature vectors to distinguish between amyloid positive and amyloid negative.

20. The medical system according to claim 14, wherein classifying the PET image as amyloid positive or amyloid negative includes at least one of:
  extracting statistics regarding the cortical profiles including a depth of a maximum or a minimum uptake value and a depth of a maximum standard deviation, the extracted statistics being used in classifying the PET images as amyloid positive or amyloid negative; and
  using a trained machine learning algorithm to extract feature vectors to distinguish between amyloid positive and amyloid negative.

* * * * *